United States Patent [19]

Meyer et al.

[11] B 3,989,708

[45] Nov. 2, 1976

[54] 2-AMINO-1,4-DIHYDROPYRIDINE DERIVATIVES

[75] Inventors: Horst Meyer; Friedrich Bossert, both of Wuppertal; Wulf Vater, Opladen; Kurt Stoepel, Wuppertal, all of Germany

[73] Assignee: Bayer Aktiengesellschaft, Leverkusen, Germany

[22] Filed: Nov. 25, 1974

[21] Appl. No.: 526,510

[44] Published under the second Trial Voluntary Protest Program on January 20, 1976 as document No. B 526,510.

Related U.S. Application Data

[62] Division of Ser. No. 390,194, Aug. 21, 1973, Pat. No. 3,862,162.

[30] Foreign Application Priority Data

Aug. 31, 1972  Germany............................ 2242786

[52] U.S. Cl..................... 260/294.8 D; 260/294.8 F; 260/294.8 G; 260/294.9; 260/295.5 R; 260/295.5 B

[51] Int. Cl.$^2$...................................... C07D 213/55
[58] Field of Search............. 260/294.8 D, 294.8 G, 260/295.5 R, 295.5 B, 294.9

[56] References Cited

UNITED STATES PATENTS

| | | | |
|---|---|---|---|
| 3,775,422 | 11/1973 | Bossert et al. | 260/294.9 |
| 3,799,934 | 3/1974 | Meyer et al. | 260/295.5 R |
| 3,799,936 | 3/1974 | Meyer et al. | 260/295.5 R |

*Primary Examiner*—Alan L. Rotman

[57] ABSTRACT

2-Amino-1,4-dihydropyridines bearing an ester carbonyl function in the 3-position, being optionally substituted by lower alkyl in the 5-position, and being substituted in the 4- and 6-positions by lower alkyl, phenyl, substituted phenyl or a heterocyclic group are antihypertensive agents and coronary vessel dilators. The compounds, of which 2-amino-6-methyl-4-(3-chlorophenyl)-1,4-dihydropyridine-3 carboxylic acid ethyl ester is a representative embodiment, are prepared through condensation of an α-B-unsaturated ketone and an amidine.

2 Claims, No Drawings

2-AMINO-1,4-DIHYDROPYRIDINE DERIVATIVES

This is a division of application Ser. No. 390,194 filed Aug. 21, 1973, now U.S. Pat. No. 3,862,162 issued Jan. 21, 1975.

DETAILED DESCRIPTION

The present invention pertains to 2-amino-1,4-dihydropyridine derivatives, to processes for their production and use and to pharmaceutical compositions containing such compounds and useful as antihypertensive agents and coronary vessel dilators.

In particular, the present invention pertains to compounds of the formula:

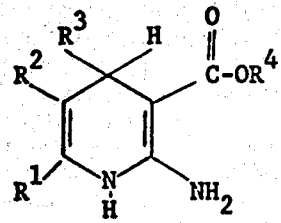

wherein
each of $R^1$ and $R^3$, independently of the other, is lower alkyl; phenyl; phenyl substituted by one to three substituents selected from the group consisting of chloro, fluoro, bromo, nitro, lower alkyl, lower alkoxy, lower alkylthio, cyano, carbo(lower alkoxy) or trifluoromethyl; pyridyl; naphthyl; thenyl; furyl; or quinolyl;
$R^2$ is hydrogen or lower alkyl; and
$R^4$ is lower alkyl, lower alkenyl, or (lower alkoxy) lower alkyl.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec.butyl, tert.butyl, pentyl, isopentyl, neopentyl, tert.pentyl, hexyl, and the like.

The term lower alkenyl denotes a univalent branched or straight hydrocarbon chain containing from 2 to 6 carbon atoms and ethylenic unsaturation as, for example, vinyl, allyl, isopropenyl, 2-butenyl, 3-methyl-2-butenyl, 2-pentenyl, 3-pentenyl, 2-hexenyl, 4-hexenyl, and the like.

The term lower alkoxy denotes a lower alkyl group bound to the remainder of the molecule through an ethereal oxygen atom as, for example, methoxy, ethoxy, propoxy, isopropoxy, butoxy, isobutoxy, pentoxy and hexoxy.

The term lower alkylthio denotes a branched or straight hydrocarbon chain bound to the remainder of the molecule through a divalent sulfur as, for example, methylthio, ethylthio, propylthio, isopropylthio, butylthio, and the like.

The term halogen denotes the substituents fluoro, chloro, bromo and iodo.

As indicated, the present invention also pertains to the physiologically acceptable non-toxic acid addition salts of these basic compounds. Such salts include those derived from organic and inorganic acids such as, without limitation, hydrochloric acid, hydrobromic acid, phosphoric acid, sulfuric acid, methane sulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

According to the present invention, the foregoing compounds are prepared by reacting an α,β-unsaturated ketone compound of the formula:

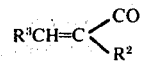

wherein $R^1$, $R^2$ and $R^3$ are as herein defined, with an amidine of the formula:

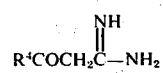

in which $R^4$ is as herein defined. The condensation proceeds smoothly in good yields simply by heating the two components, generally in the presence of an inert organic solvent such as methanol, ethanol, propanol and similar alkanols, ethers such as dioxane and diethyl ether, glacial acetic acid, pyridine, dimethylformamide, dimethylsulfoxide, acetonitrile and the like. The reaction is conducted at temperatures of from 20° to 200°C, conveniently at the boiling point of the solvent, and while elevated pressure may be utilized, normal atmospheric pressure is generally satisfactory. The reactants are employed in substantially equimolar amounts. The amidine reactant can be employed as the free base or in the form of a salt such as the hydrohalide salts with the amidine being liberated from the salt through treatment with a basic agent such as an alkali metal alkoxide.

It is rather surprising that the above described condensation produces the desired compounds in such good yields and with such high purity for while it is known that a benzylideneacetoacetic acid ester can be condensed with an amino crotonic acid ester to yield a 1,4-dihydropyridine (Knoevenagel, Ber. 31, 743, 1898), it would be expected from, for example, Silversmith, J. Org. Chem. 27, 4090 (1952) that the addition of an amidine to an α,β-unsaturated keto compound would yield the dihydropyrimidine derivative rather than the dihydropyridine derivative.

Many of the α,β-unsaturated ketone compounds utilized as one of the reactants are known to the art and the others can either be generated in situ as herein described or prepared according to methods well known to the art, see for example Org. Reaction XV, 204 et seq. (1967). Typical of this reactant are the following compounds:
benzylideneacetone,
benzylideneacetophenone,
2-chlorobenzylideneacetone,
3-chlorobenzylideneacetone,
4-chlorobenzylideneacetone,
2,4-dichlorobenzylideneacetone,
2,6-dichlorobenzylideneacetone,
2-methoxybenzylideneacetone,
2-methylbenzylideneacetone,
3-methylbenzylideneacetone,
4-methylbenzylideneacetone,
2-nitrobenzylideneacetone,
3-nitrobenzylideneacetone,
4-nitrobenzylideneacetone,
3-nitro-4-chlorobenzylideneacetone,
2-methylmercaptobenzylideneacetone, 2-trifluoromethylbenzylideneacetone,
3-trifluoromethylbenzylideneacetone,
4-trifluoromethylbenzylideneacetone,
2-cyanobenzylideneacetone,
3-cyanobenzylideneacetone,
4-cyanobenzylideneacetone,
3-carbethoxybenzylideneacetone,
1-phenyl-2-methyl-but-1-en-3-one,
1-(α-pyridyl)-but-1-en-3-one,
1-(β-pyridyl)but-1-en-3-one,
1-(2-furyl)-but-1-en-3-one,
1-(2-thenyl)-but-1-en-3-one,
1-(α-naphthyl)-but-1-en-3-one,
1-(β-naphthyl)-but-1-en-3-one,
1-(2-quinolyl)-but-1-en-3-one,
1-(4-quinolyl)-but-1-en-3-one,
1-(3-nitrophenyl)-2-isopropylbut-1-en-3-one,
1-phenyl-4,4-dimethylbut-1-en-3-one,
2-chlorobenzylideneacetophenone,
3-chlorobenzylideneacetophenone,
4-chlorobenzylideneacetophenone,
2-nitrobenzylideneacetophenone,
3-nitrobenzylideneacetophenone,
4-nitrobenzylideneacetophenone,
2-trifluoromethylbenzylideneacetophenone,
3-trifluoromethylbenzylideneacetophenone,
4-trifluoromethylbenzylideneacetophenone,
benzylidene-4-fluoroacetophenone,
3-bromobenzylideneacetophenone,
3-chlorobenzylidene-4-chloroacetophenone,
benzylidene-2-nitroacetophenone,
4-nitrobenzylidene-4-bromoacetophenone,
2-nitrobenzylidene-4-nitroacetophenone,
2-nitrobenzylidene-2-nitroacetophenone,
4-nitrobenzylidene-3-nitroacetophenone,
3,4,5-trimethoxybenzylideneacetophenone,
2-methylmercaptobenzylideneacetophenone,
4-methylmercaptobenzylideneacetophenone,
2-chlorobenzylidene-4-trifluoromethylacetophenone,
3-chlorobenzylidene-4-methylmercaptoacetophenone,
1-(α-pyridyl)-3-phenyl-prop-1-en-3-one,
1-phenyl-3-(α-pyridyl)-prop-1-en-3-one,
1-(β-pyridyl)-3-phenylprop-1-en-3-one,
1-phenyl-3-(2-thenyl)-prop-1-en-3-one,
1-phenyl-3-(2-furyl)-prop-1-en-3-one,
1,3-diphenyl-2-methyl-prop-1-en-3-one,
1,3-diphenyl-2-isopropyl-prop-1-en-3-one,
1-methyl-b 3-phenyl-prop-1-en-3-one,
1-cyclohexyl-3-phenyl-prop-1-en-3-one,
1-isopropyl-3-phenylprop-1-en-3-one,
1-($\Delta^3$-cyclohexenyl)-3-phenylprop-1-en-3-one.

The amidine reactants are similarly known or can be readily produced according to known methods, see for example McElvain et al., J.A.C.S., 73, 2760 (1951). Typical of these reactants are the following:
amidinoacetic acid methyl ester,
amidinoacetic acid ethyl ester,
amidinoacetic acid n-propyl ester,
amidinoacetic acid isopropyl ester,
amidinoacetic acid cyclohexyl ester,
amidinoacetic acid β-methoxyethyl ester,
amidinoacetic acid α-ethoxyethyl ester,
amidinoacetic acid β-ethoxyethyl ester,
amidinoacetic acid propargyl ester, and
amidinoacetamide.

As noted above, the compounds of the present invention demonstrate the ability to reduce blood pressure and to effect a dilation of the coronary vessels. They can accordingly be used where either or both of these effects are desired. Thus upon parenteral, oral or sublingual administration, the compounds produce a distinct and long lasting dilation of the coronary vessels which is intensified by a simultaneous nitritelike effect of reducing the load on the heart. The effect on heart metabolism is thus one of energy saving. In addition, the compounds lower the blood pressure of normotonic and hypertonic animals and can thus be used as antihypertensive agents. These properties can be conveniently observed in well known laboratory models. Thus for example the coronary vessel dilation effect of 2-amino-6-phenyl-4-(2-chlorophenyl)-1,4-dihydropyridine-3-carboxylic acid ethyl ester can be observed, by measuring the increase in oxygen saturation in the coronary sinus in the narcotized, heart catheterized dog, at an I.V. dose as low as 0.2 mg/kg.

The hypotensive activity of the present compounds can be observed by measuring the blood pressure of hypertensive rats following administration of the compounds. The following table demonstrates the dose which results in at least a 15 mm Hg reduction in blood pressure of such animals:

| Compound | Dose (mg/kg) |
|---|---|
| 2-amino-6-methyl-4-(2-chlorophenyl)-1,4-dihydropyridine-3-carboxylic acid ethyl ester | 31.5 |
| 2-amino-6-methyl-4-(2-chlorophenyl)-1,4-dihydropyridine-3-carboxylic acid isopropyl ester | 10.0 |

In addition to the effect on blood pressure and coronary vessels, the compounds also lower the excitability of the stimulus formation and excitation conduction system within the heart so that an antifibrillation action is observed at therapeutic doses. The tone of the smooth muscle of the vessels is also greatly reduced. This vascular-spasmolytic action can be observed in the entire vascular system as well as in more or less isolated and circumscribed vascular regions such as the central nervous system. In addition, a strong muscular-spasmolytic action is manifested in the smooth muscle of the stomach, the intestinal tract, the urogenital tract and the respiratory system. Finally, there is some evidence that the compounds influence the cholesterol level and lipid level of the blood. These effects complement one another and the compounds are thus highly desirable as pharmaceutical agents to be used in the treatment of hypertension and conditions characterized by a constriction of the coronary blood vessels.

Pharmaceutical compositions for effecting such treatment will contain a major or minor amount, e.g. from 95 to 0.5 percent, of at least one 2-amino-1,4-dihydropyridine as herein defined in combination with a pharmaceutical carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three four or more single doses or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three of four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the daily dose will be from about 0.001 to about 2 mg/kg, preferably 0.005 to 1.0 mg/kg, when administered parenterally and from about 0.1 to about 20 mg/kg, preferably 0.5 to 10 mg/kg, when administered orally. In some instances a sufficient therapeutic effect can be obtained at lower doses while in others, larger doses will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The midicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

The following examples will serve to further typify the nature of the present invention through the presentation of specific embodiments. These examples should not be construed as a limitation on the scope of Applicants' invention since the subject matter regarded as the invention is set forth in the appended claims.

EXAMPLE 1

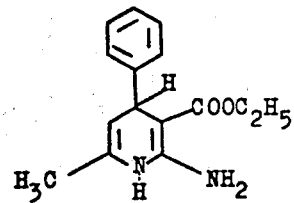

Boiling a solution of 14.6 g of benzylideneacetone and 13.0 g of amidinoacetic acid ethyl ester in 150 ml of ethanol for 2 hours yields 2-amino-6-methyl-4-phenyl-1,4-dihydropyridine-3-carboxylic acid ethyl ester of melting point 150°C (ethanol). Yield: 73 percent of theory.

EXAMPLE 2

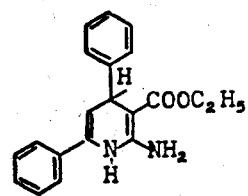

Upon heating a solution of 20.8 of benzylideneacetophenone and 13.0 g of amidinoacetic acid ethyl ester in 250 ml of ethanol for 2 hours, 2-amino-4,6-diphenyl-1,4-dihydropyridine-3-carboxylic acid ethyl ester of melting point 159°C (ethanol) is obtained. Yield: 69 percent of theory.

EXAMPLE 3

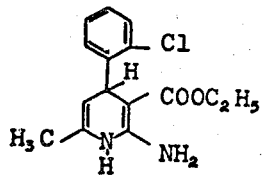

Upon boiling a solution of 18.1 g of 2-chlorobenzylideneacetone and 13.0 g of amidinoacetic acid ethyl ester in 150 ml of ethanol for 2 hours, 2-amino-6-methyl-4-(2-chlorophenyl)-1,4-dihydropyridine-3-carboxylic acid ethyl ester of melting point 171°C (ethanol) is obtained. Yield: 62 percent of theory.

EXAMPLE 4

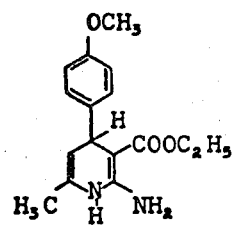

Heating a solution of 17.5 g of 4-methoxybenzylideneacetone and 13.0 g of amidinoacetic acid ethyl ester in 150 ml of ethanol for 2 hours yields 2-amino-6-methyl-4-(4-methoxyphenyl)-1,4-dihydropyridine-3-carboxylic acid ethyl ester of melting point 160°–161°C (ethanol). Yield: 52 percent theory.

EXAMPLE 5

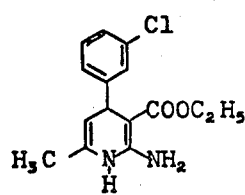

After heating a solution of 18.1 g of 3-chlorobenzylideneacetone and 13.0 g of amidinoacetic acid ethyl ester in 150 ml of ethanol for 3 hours, 2-amino-6-methyl-4-(3-chlorophenyl)-1,4-dihydropyridine-3-carboxylic acid ethyl ester of melting point 140°C (isopropanol) is obtained. Yield: 56 percent of theory.

EXAMPLE 6

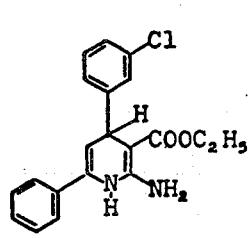

Upon heating a solution of 24.3 g of 3-chlorobenzylideneacetophenone and 13.0 g of amidinoacetic acid ethyl ester in 250 ml of ethanol for 4 hours, 2-amino-6-phenyl-4-(3-chlorophenyl)-1,4-dihydropyridine-3-carboxylic acid ethyl ester of melting point 161°C is obtained. Yield: 73 percent of theory.

EXAMPLE 7

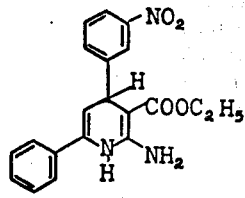

Upon boiling a solution of 25.3 g of 3-nitrobenzylideneacetophenone and 13.0 g of amidinoacetic acid ethyl ester in 250 ml of ethanol for 2 hours, 2-amino-6-phenyl-4-(3-nitrophenyl)-1,4-dihydropyridine-3-carboxylic acid ethyl ester of melting point 171°–172°C (ethanol) is obtained. Yield: 71 percent of theory.

EXAMPLE 8

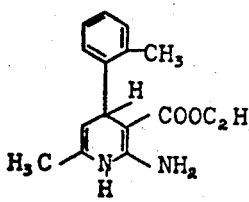

Upon heating a solution of 16.0 g of 2-methylbenzylideneacetone and 13.0 of amidinoacetic acid ethyl ester in 150 ml of ethanol for 2 hours, 2-amino-6-methyl-4-(2-methylphenyl)-1,4-dihydropyridine-3-carboxylic acid ethyl ester of melting point 159°C (isopropanol) is obtained. Yield: 61 percent of theory.

EXAMPLE 9

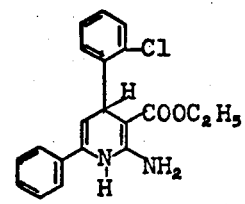

Upon boiling a solution of 24.3 g of 2-chlorobenzylideneacetophenone and 13.0 g of amidinoacetic acid ethyl ester in 250 ml of ethanol for 3 hours, 2-amino-6-phenyl-4-(2-chlorophenyl)-1,4-dihydropyridine-3-carboxylic acid ethyl ester of melting point 196°C (alcohol) is obtained. Yield: 68 percent of theory.

EXAMPLE 10

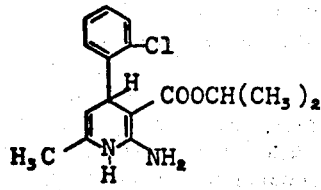

Upon heating a solution of 18.1 g of 2-chlorobenzylideneacetone and 14.1 g of amidinoacetic acid isopropyl ester in 200 ml of isopropanol for 3 hours, 2-amino-6-methyl4-(2-chlorophenyl)-1,4-dihydropyridine-3-carboxylic acid isopropyl ester of melting point 161°C (isopropanol) is obtained. Yield: 51 percent of theory.

We claim:
1. A compound of the formula:

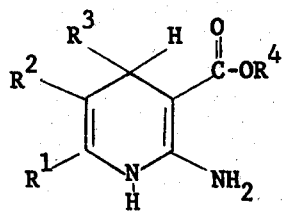

wherein R¹ is lower alkyl or phenyl;
R³ is pyridyl, naphthyl; thienyl or furyl;
R² is hydrogen or lower alkyl; and
R⁴ is lower alkyl, alkenyl of 2 to 4 carbon atoms, or lower alkyl.

2. A compound of the formula:

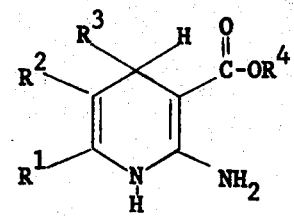

wherein
R¹ is chlorophenyl, fluorophenyl, bromophenyl, nitrophenyl, lower alkoxyphenyl, lower alkylthiophenyl, cyanophenyl, carbo(lower alkoxy)phenyl, trifluoromethylphenyl; naphthyl; pyridyl; thienyl or furyl;
R² is hydrogen or lower alkyl;
R³ is lower alkyl, phenyl, chlorophenyl, fluorophenyl, bromophenyl, nitrophenyl, lower alkylphenyl, lower alkoxyphenyl, lower alkylthiophenyl, cyanophenyl, carbo(lower alkoxy)phenyl, trifluoromethylphenyl; naphthyl; pyridyl; thienyl or furyl; and
R⁴ is lower alkyl, alkenyl of 2 to 4 carbon atoms or (lower alkoxy)lower alkyl.

* * * * *